(12) United States Patent
Subramaniam et al.

(10) Patent No.: US 6,448,454 B1
(45) Date of Patent: Sep. 10, 2002

(54) CATALYTIC OXIDATION OF ORGANIC SUBSTRATES BY TRANSITION METAL COMPLEXES IN ORGANIC SOLVENT MEDIA EXPANDED BY SUPERCRITICAL OR SUBCRITICAL CARBON DIOXIDE

(75) Inventors: Bala Subramaniam; Daryle H. Busch; Ghezai T. Musie; Ming Wei, all of Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 09/545,214

(22) Filed: Apr. 7, 2000

(51) Int. Cl.$^7$ ............... C07C 37/00; C07C 45/00; C07C 49/105; C07B 41/04; C07B 41/02
(52) U.S. Cl. .............. 568/800; 568/322; 568/362; 568/377; 568/398.8; 568/910.5
(58) Field of Search .............. 568/910.5, 800, 568/322, 362, 377, 398.8, 698, 860, 858; 560/239; 522/5, 79, 178

(56) References Cited

U.S. PATENT DOCUMENTS

| | | |
|---|---|---|
| 5,210,336 A | 5/1993 | Gaffney et al. |
| 5,831,116 A | 11/1998 | Wang et al. |
| 5,872,157 A | 2/1999 | DeSimone et al. |

OTHER PUBLICATIONS

Birnbaum et al.; J. Mol. Catal., A 139: 11–24 (1999).*
Birnbaum et al.; *J. Mol. Catal.*, A 139:11–24 (1999).
Srinivas et al.; *Ind. Eng. Chem. Res.*, 33, 3118–3124 (1994).
Wu et al.; *Chem. Lett.*, 1045–1046 (1997).
Murahashi et al.; *Tetrahedron Lett.*, 36:8059–8062 (1995).
Dooley et al.; *Ind. Eng. Chem. Res.*, 26:1910–1916 (1987).
Haas et al.; *Organometallics*, 17:4454–4460 (1998).
Perisi et al.; *Chem. Commum.*, 10151 (1998).

* cited by examiner

Primary Examiner—Samuel Barts
Assistant Examiner—Elvis O. Price
(74) Attorney, Agent, or Firm—Hovey Williams LLP

(57) ABSTRACT

Improved oxidation methods are provided wherein a reaction mixture comprising a substrate to be oxidized (e.g., phenols, alkenes) and an oxidation catalyst (typically dispersed in an organic solvent system) is supplemented with a compressed gas which expands the reaction mixture, thus accelerating the oxidation reaction. In preferred practice pressurized subcritical or supercritical carbon dioxide is used as the expanding gas, which is introduced into the reaction mixture together with an oxidizing agent. The inventive methods improve the substrate conversion and product selectivity by increasing the solubility of the oxidizing agent in the reaction mixture.

28 Claims, 12 Drawing Sheets

△ % selectivity in scCO$_2$ at 70°C

▲ % conversion in scCO$_2$ at 70°C

■ % conversion in CO$_2$-expanded CH$_3$CN media at 60°C

□ % selectivity in CO$_2$-expanded CH$_3$CN media at 60°C

*Fig.* 7

▲ % conversion in scCO$_2$ at oxygen:substrate molar ratio of 4

△ % selectivity in scCO$_2$ at oxygen:substrate molar ratio of 4

■ % conversion in two-fold expanded CH$_3$CN solvent at oxygen:substrate molar ratio of 2

□ % selectivity in two-fold expanded CH$_3$CN solvent at oxygen:substrate molar ratio of 2

■ two-fold CO$_2$-expanded CH$_3$CN phase at oxygen:substrate molar ratio of 2

▲ scCO$_2$ phase at oxygen:substrate molar ratio of 4

▲ % conversion using Co(salen)
△ % selectivity using Co(salen)
■ % conversion using Co(salen*)
□ % selectivity using Co(salen*)

CATALYTIC OXIDATION OF ORGANIC SUBSTRATES BY TRANSITION METAL COMPLEXES IN ORGANIC SOLVENT MEDIA EXPANDED BY SUPERCRITICAL OR SUBCRITICAL CARBON DIOXIDE

BACKGROUND OF THE INVENTION

1. Field of the Invention

The present invention is broadly concerned with processes for oxidizing organic substrates (and oxidation reaction mixtures) wherein an oxidizable substrate/oxidation catalyst reaction mixture is volumetrically expanded-through use of a compressed gas so as to facilitate and enhance oxidation of the substrate. More particularly, the invention in preferred forms pertains to oxidation reaction mixtures including an organic solvent system together with the substrate and oxidation catalyst, wherein an inert gas such as carbon dioxide is introduced into the reaction mixture for volumetric expansion thereof, followed by introduction of an oxidizing agent; volumetric expansion serves to accelerate the oxidation of the substrate.

2. Description of the Prior Art

During conventional homogeneous catalytic oxidation of organic substrates in organic solvents, the catalyst and substrate are dissolved in a suitable organic solvent medium such as methylene chloride or acetonitrile to form the initial reaction mixture. Dioxygen is then bubbled through the reaction mixture. The reaction proceeds in the "open" system until the desired conversion is achieved. However, these conventional processes suffer from several drawbacks. First, the upper temperature limit is constrained by the boiling point of the substrate and/or solvent medium because, at high temperatures, the resulting vapors can form explosive mixtures. Hence, the reaction must be carried out at lower temperatures whereat vapor pressures are low.

Another problem with prior art processes is that, at such low temperatures, reaction rates are low making large batch times or reactor volumes necessary during continuous processing. This large hold-up of hazardous materials in a reactive environment is unsafe.

The prior art processes are also lacking in that the solubility of dioxygen in the reaction mixture is so low that it is often the rate-determining step of the reaction. The lack of sufficient oxygen solubility can also adversely affect catalyst performance in selectively forming products. That is, the catalyst may be intrinsically superior for activating molecular oxygen, but the limited solubility of oxygen in the reaction mixture prevents the catalyst from exhibiting its full potential.

In recent years, supercritical $CO_2$ has been employed as a replacement for organic solvents in homogeneous catalytic oxidation systems. Supercritical $CO_2$ has also been exploited to overcome $O_2$ solubility limitations. However, extremely high pressures are required to solubilize catalysts such as transition metal complexes in the supercritical $CO_2$-based reaction mixture. Moreover, the conversions attained with supercritical $CO_2$-based systems are usually lower than those obtained with conventional solvents. Thus, the only real advantage with prior art supercritical $CO_2$-based systems is the replacement of conventional organic solvents with an environmentally-benign solvent.

SUMMARY OF THE INVENTION

The present invention overcomes the problems of the prior art and provides novel oxidation processes and reaction mixtures wherein the oxidation reaction mixtures broadly including an oxidizable substrate and an oxidation catalyst are supplemented with a compressed gas such as carbon dioxide so as to volumetrically expand the reaction mixture, thereby facilitating and accelerating oxidation. Although the expansion gas may also serve as the oxidizing agent, typically an oxidizing agent separate from the inert gas is employed. Also, the reaction mixtures generally include an organic solvent system.

In more detail, the inventive processes comprise forming a reaction mixture including an oxidizable substrate and an oxidation catalyst, volumetrically expanding the reaction mixture, and thereafter causing the oxidation reaction to occur. The volumetric expansion is normally carried out by introducing a compressed gas into the reaction mixture. If the inert gas is also an oxidizing agent for the substrate (e.g., when $N_2O$ is employed), the oxidation reaction proceeds. However, where an inert gas such as $CO_2$ is employed, a separate oxidizing agent is introduced into the expanded reaction mixture to initiate the oxidation reaction.

In preferred forms, the starting reaction mixture includes an organic solvent system, with the substrate and catalyst dispersed (and preferably solubilized) in the solvent system. Such an organic system is usually made up of solvents selected from the group consisting of acetonitrile, methylene chloride, dimethyl sulfoxide, acetone, hexane, chloroform, toluene, dichloroethane and mixtures thereof. A solvent system made up of a mixture of acetonitrile and methylene chloride is particularly preferred.

A variety of oxidation catalysts can be used in the invention. For example, transition metal complexes of Fe, Mn, Co, Cu, Ni, V, Cr, Mo, W, Re, Ru, and Rh and mixtures thereof can be used to good effect. Especially preferred catalysts are those selected from the group consisting of Co(salen*), Co(salen), and PFTPPFeCl. Similarly, the class of useable substrates is very large, and may be selected from the group consisting of the phenols, alkenes cycloalkenes, alkanes and alcohols, and mixtures thereof. The substrate may be present as a gas, a liquid, or as a solid.

The expanding gas is generally selected from the group consisting of carbon dioxide, $N_2O$, Xenon, and $SF_6$, although for reasons of cost and ease of use, pressurized subcritical or supercritical carbon dioxide is usually the gas of choice. The expanding gas is present in the reaction mixture at a level below that which will cause the catalyst to precipitate; that is, the catalyst is usually least soluble component of the reaction mixture, and for good results it should remain dispersed. Therefore, the expanding gas is introduced at levels which will maintain catalyst suspension. These level of course vary depending upon the components of the reaction mixture, and especially the catalyst. It is therefore usually necessary to preliminarily determine the extent of expanding gas supplementation which can be accommodated with each individual reaction mixture.

In most instances the expanded reaction mixture will have a lower density than the reaction mixture prior to introduction of the expanding gas. In such cases, the extent of lowering of the density is an alternate measure of the amount of expanding gas which can be used before the catalyst begins to precipitate.

A number of oxidizing agents can be used as required in the methods of the invention. The most common oxidation agents are selected from the group consisting of air, oxygen, ozone, $N_2O$ and mixtures thereof. Molecular oxygen is usually the preferred agent.

The processes of the invention are carried out in a closed system at superatmospheric pressures. These pressures range from about 20–250 bar, more preferably from about 50–200 bar. The oxidation reactions can be carried out over a wide temperature range, usually from about −70 to 250° C., more preferably from about 15–100° C.

The inventive processes are particularly useful for oxidizing phenols and alkenes using a transition metal complex as the oxidizing catalyst. Examples of such catalysts include [N,N'-Bis(3,5-di-tert-butylsalicylidene) 1,2-cyclohexanediarninato(2-)]cobalt(II) (hereinafter referred to as "Co(salen*)") and [N,N'-ethylenebis(salicylidene-aminato(2-)]cobalt(II) (hereinafter referred to as "Co(salen)") and [5,10,15,20-tetrabis(pentafluorophenyl) porphyrin] iron(III) chloride (PFTPPFeCl).

The inventive processes have numerous significant advantages over prior art including: apply to a wide range of catalyst and substrates; require low quantities of organic solvents; increase oxygen solubility in the reaction mixture thus improving substrate conversion and selectivity; can be carried out at lower operating pressures than prior art supercritical $CO_2$-based reaction systems; and are safer to carry out than prior art processes.

DETAILED DESCRIPTION OF THE PREFERRED EMBODIMENTS

EXAMPLES

The following examples set forth preferred methods in accordance with the invention. It is to be understood, however, that these examples are provided by way of illustration and nothing therein should be taken as a limitation upon the overall scope of the invention.

Example 1

Homogeneous Expansion of Organic Solvents Containing Dissolved Catalyst

Figure 1:
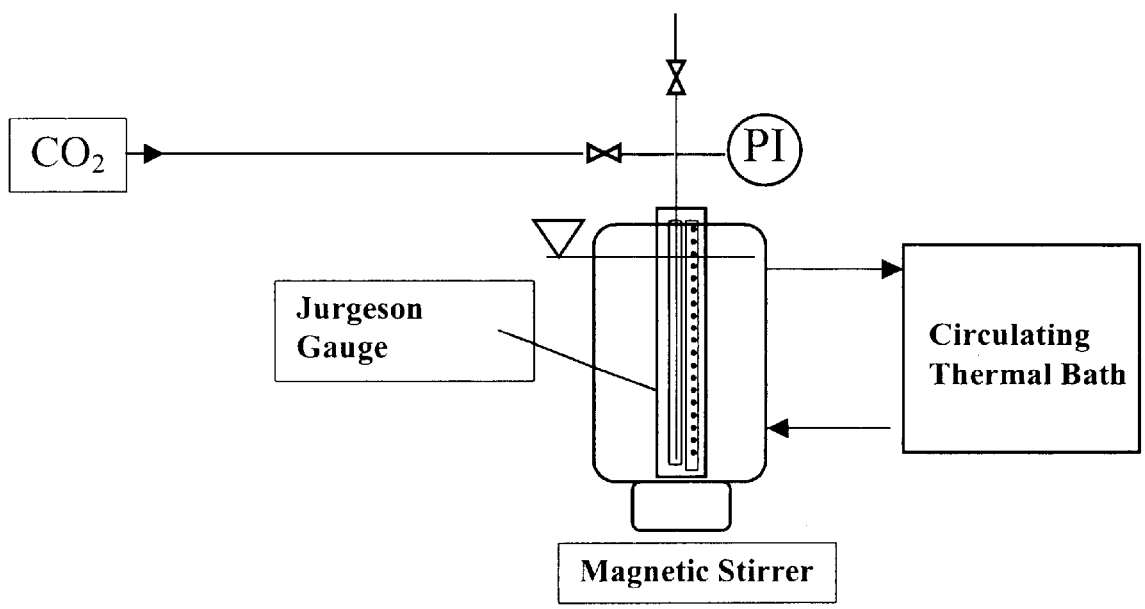
FIG. 1 is a schematic illustration of an experimental set-up for analyzing the volumetric expansion of a catalyst-containing organic solvent by $CO_2$.

In this study, the solubility of various catalysts in $CO_2$-expanded organic solvents (e.g. acetonitrile and methylene chloride) was determined. FIG. 1 schematically depicts the experimental setup utilized for measuring the volumetric expansion by $CO_2$ of organic solvents having different concentrations of transition metal catalysts dissolved therein. The observed height of the liquid or expanded phase in a view cell was initially calibrated against the corresponding volume of the phase. A calibration strip with volume markings (in mL) at various cell heights was then adhered directly to the cell body. For the expansion studies, a measured volume of organic solution containing a known amount of catalyst (mg/mL) was loaded into the 100 mL view cell which was interfaced with a magnetic stirrer assembly. The total pressure and temperature in the cell were continuously monitored, and the cell was placed in a constant temperature bath.

The vapor space above the catalyst solution was initially flushed with gaseous $CO_2$. The exit line was then shut, and the initial volume of the liquid phase noted. $CO_2$ was introduced into the cell at a controlled rate until a certain pressure is reached. The system was stirred and allowed to reached equilibrium as denoted by constant pressure, temperature, and phase height readings. The $CO_2$ addition and equilibration steps were repeated at various extents of volumetric expansion (twofold, threefold, etc. as noted in the graduated strip) until the dissolved catalyst precipitated out of the expanded phase at a certain level of expansion. The actual expansion level at which the catalyst precipitated out was determined by performing smaller expansions and pressure-releases around the precipitation point. The total volume and the pressure at which precipitation occurred were registered as the maximum expansion level for an organic solution containing that concentration of the catalyst (mg/mL). Such data were acquired for each solvent/catalyst system at various reaction temperatures in order to establish maximum expansion limits with $CO_2$.

Figure 2:
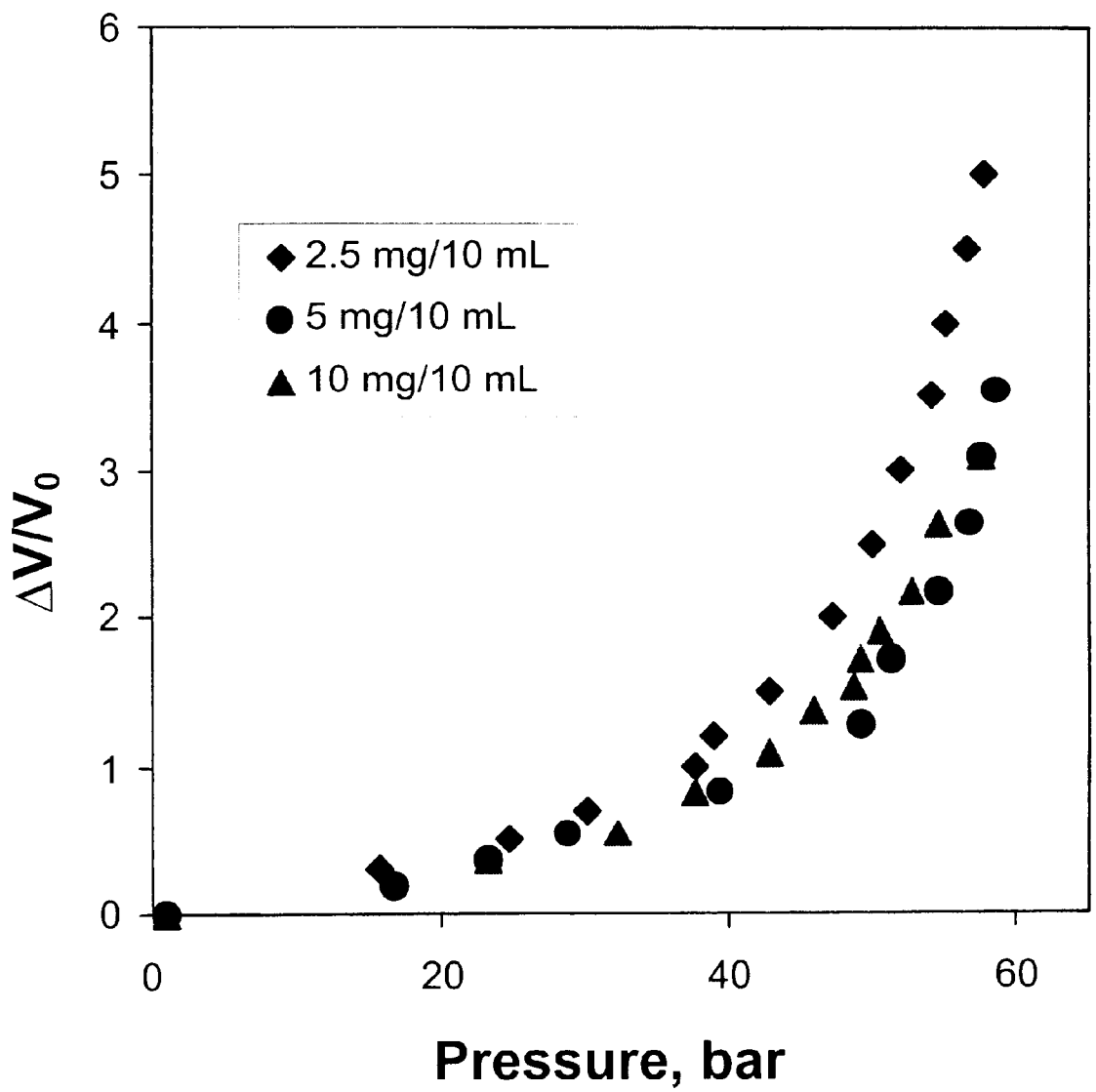
FIG. 2 is a graph depicting the expansion curves for solutions having varying concentrations of Co(salen*) in $CH_2Cl_2$ by $CO_2$ at 25° C.
Figure 3:
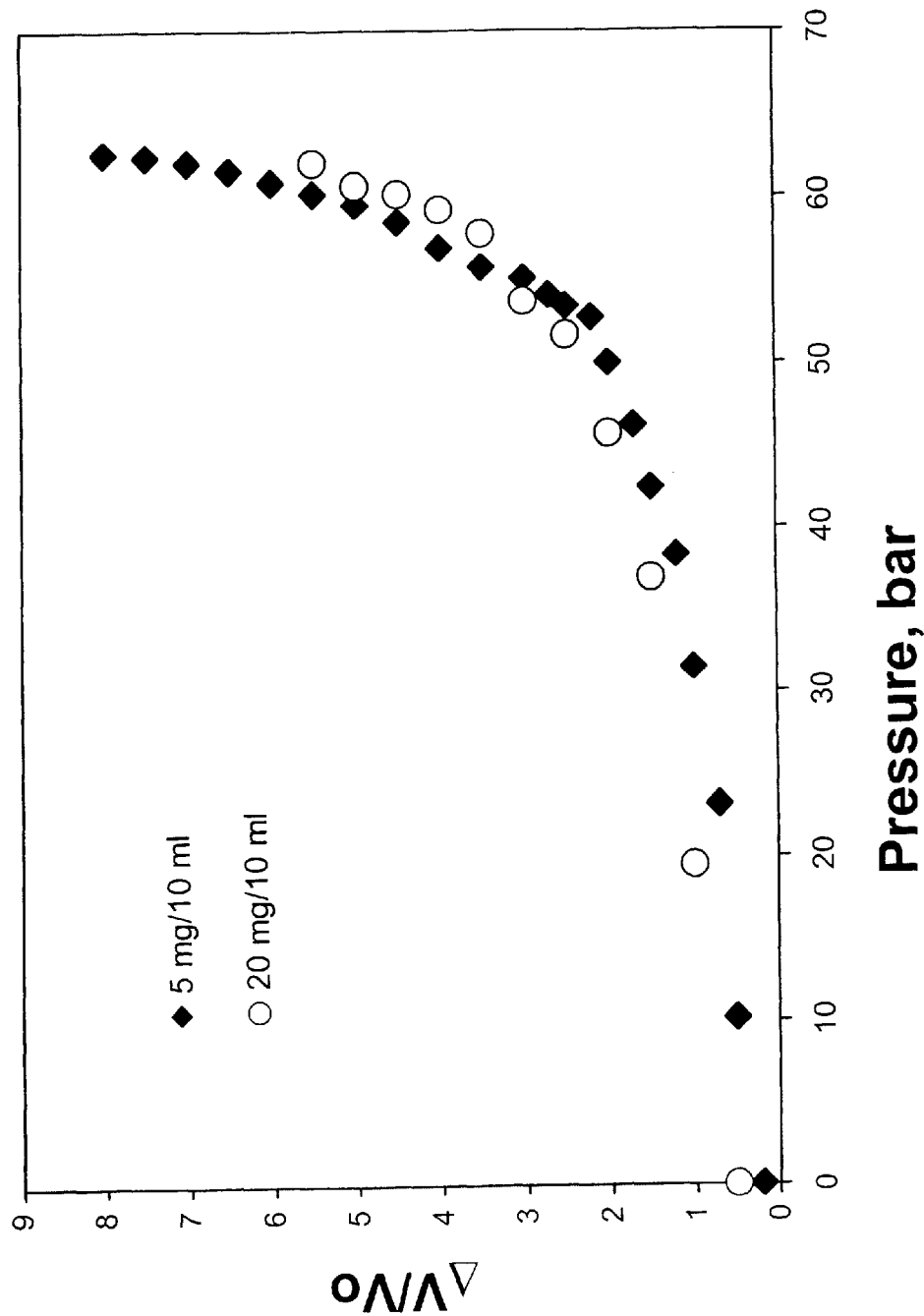
FIG. 3 is a graph depicting the relative volumetric expansion by $CO_2$ of $CH_3CN$ solutions containing varying concentrations of dichloro(4,11-dimethyl-1,4,8,11-tetraazabicyclo(6,6-hexadecane) manganese (II) (Mn $(Me_2B14N4)Cl_2$) at 25° C.
Figure 4:
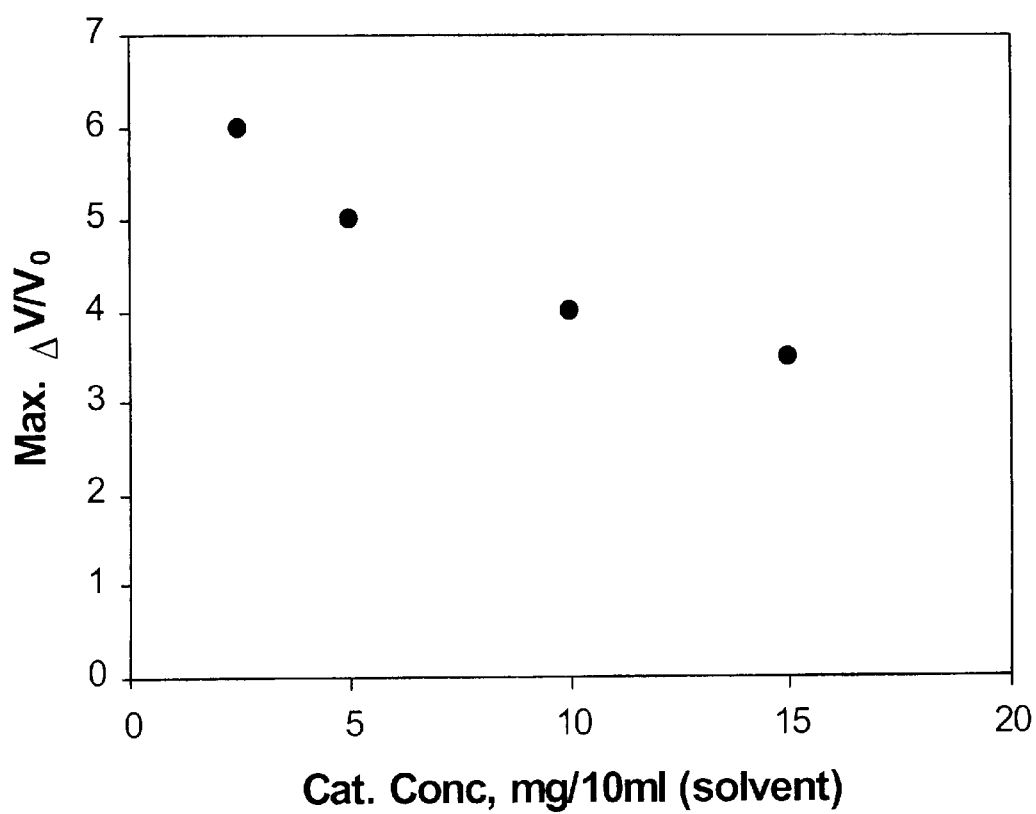
FIG. 4 is a graph depicting the maximum relative homogeneous expansion by $CO_2$ and precipitation of Co(salen*) from a $CH_2Cl_2$ solution.

FIGS. 2 and 3 are plots of the relative volumetric expansions of different solvents (methylene chloride and acetonitrile) containing various concentrations of catalysts. An example of the raw data used to generate these Figures is set forth in Table 1. Relative volumetric expansion was defined as the fractional increase in the volume of the initial solution. With $CO_2$ addition, the total pressure increases, and the volume of the homogeneous phase increases (i.e., expands) exponentially as shown in FIG. 2 and FIG. 4. The solubility of the catalyst in the expanded solvent decreased continuously, and the catalyst precipitated out at a certain value of relative expansion.

TABLE 1

Raw Data for the $CO_2$-Expansion of the
$CH_2Cl_2$ Solutions of Co(salen*)
Amount of catalyst/10 mL of solvent

| 2.5 mg | | 5.0 mg | | 10 mg | |
|---|---|---|---|---|---|
| p, bar | $\Delta V/V_0$ | p, bar | $\Delta V/V_0$ | p, bar | $\Delta V/V_0$ |
| 1.0 | 0.00 | 1.0 | 0.00 | 1.0 | 0.00 |
| 15.8 | 0.30 | 16.7 | 0.18 | 23.3 | 0.36 |
| 24.7 | 0.50 | 23.3 | 0.36 | 32.2 | 0.55 |
| 30.1 | 0.70 | 28.8 | 0.55 | 37.7 | 0.82 |
| 37.7 | 1.00 | 39.4 | 0.82 | 42.8 | 1.09 |
| 39.0 | 1.20 | 49.3 | 1.27 | 45.9 | 1.36 |
| 47.3 | 2.00 | 51.4 | 1.73 | 48.6 | 1.55 |
| 50.0 | 2.50 | 54.8 | 2.18 | 49.3 | 1.73 |
| 52.1 | 3.00 | 56.7 | 2.64 | 50.7 | 1.91 |
| 54.1 | 3.50 | 57.5 | 3.01 | 52.7 | 2.18 |
| 56.6 | 4.00 | 58.6 | 3.45 | 54.8 | 2.64 |
| 57.9 | 5.00 | — | — | 57.5 | 3.09 |

FIG. 2 shows isothermal volumetric expansion profiles at 25° C. for similar initial solution volumes of $CH_2Cl_2$ (10 mL) but with three different concentrations of dissolved catalyst [N,N'-Bis(3,5-di-tert-butylsalicylidene)1,2-cyclohexanediaminato (2-)] cobalt(II) (hereinafter referred to as "Co(salen*)"). As shown in FIG. 2, the maximum value of homogenous expansion before catalyst precipitation occurs (termed as the "maximum homogeneous expansion limit") is higher for a dilute solution than for a more concentrated solution. For example, the 2.5 mg/10 mL solution of the Co(salen*) catalyst has a maximum expansion limit of 5 as compared to 3 for the 10.0 mg/10 mL solution. The relationship between the maximum homogeneous expansion limit and solution concentration is depicted in FIG. 3.

The maximum homogeneous expansion limit also depends upon the catalyst/solvent combination. As can be seen in comparing FIGS. 2 and 4, while the maximum relative expansion of the 2.5 mg/10 mL $CH_2Cl_2$ solution of the cobalt Schiff base complex Co(salen*) is 3, the corresponding expansion is 8 for the same concentration of dichloro(4,11-dimethyl-1,4,8,11-tetraazabicyclo[6.6.2]-hexadecane manganese (II) complex in acetonitrile. Clearly, such volumetric expansion studies at reaction temperatures are essential for every reaction system to determine the maximum limit of solvent expansion by $CO_2$ before the catalyst precipitates out.

Example 2

Homogeneous Catalytic Oxidation of Substituted Phenols by Transition Metal Complexes Activation of $O_2$ by reversible coordination of cobalt and other transition metal complexes and their transfer to organic substrates is of considerable importance in applications of organic synthesis and in furthering our understanding of oxidation in biological systems. For example, cobalt (II) Schiff-base complexes are known to catalyze the oxidation of phenols and other organic substrates in different organic solvents. The limited solubility and the transport limitations of oxygen in organic solvents have hindered the efficiency of these catalysts. Supercritical $CO_2$ and expanded phase organic solvent systems appear to have the potential to alleviate these limitations, and thus are attractive solvent systems for oxidation. Because of its complete miscibility with $O_2$, supercritical $CO_2$ provides high concentrations of oxidant and thus eliminates mass transfer limitations. However, the required high temperatures and pressures for solubilizing transition metal catalysts in supercritical $CO_2$ makes the solvent less attractive for industrial application. On the other hand, the $CO_2$-expanded reaction media can be operated at far lower pressures and at a wider range of temperatures.

The catalytic oxidation of DTBP by Co(salen) and Co(salen*) (see Scheme 1), were systematically studied in supercritical $CO_2$, $CO_2$-expanded, and neat organic solvents.

Scheme 1
Oxidation of 2,6-Di-tert-Butylphenol

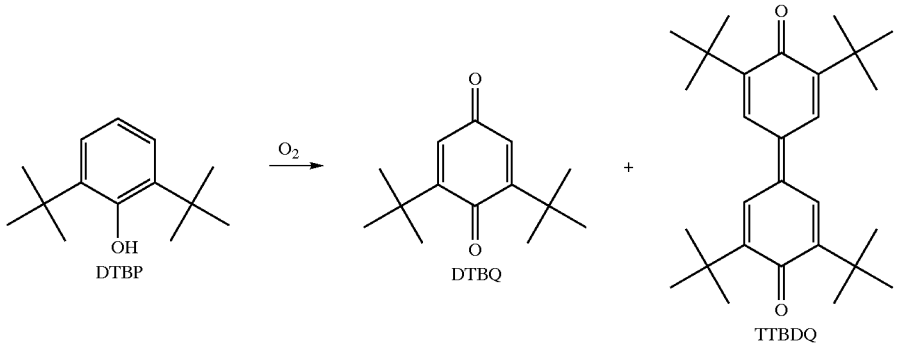

-continued

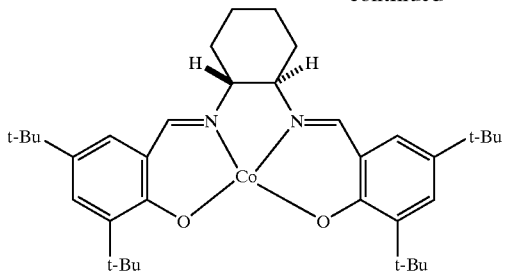

Co(Salen*) = [N,N'-Bis(3,5-di-tert-butylsalicylidene)1,2-cyclohexanediaminato(2-)]coba lt(II)

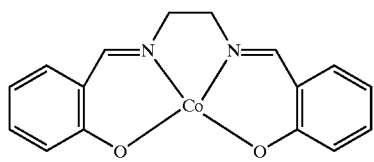

Co(Salen) = [N,N'-ethylenebis(salicylideneaminato(2-)]cobalt(II)

Figure 5:
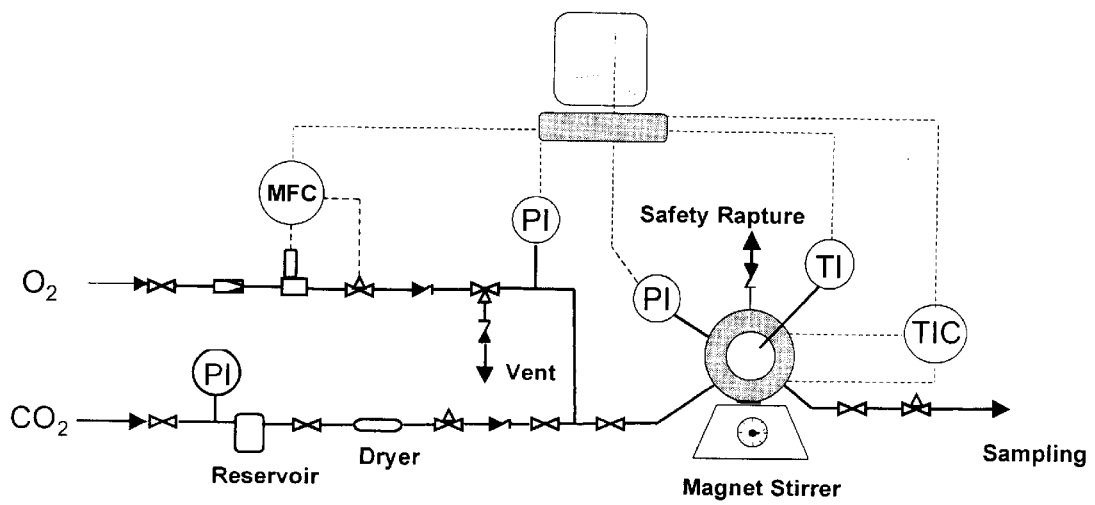
FIG. 5 is a schematic illustration of a view cell reactor set-up for analyzing catalytic oxidations in $CO_2$-expanded solvent media.

FIG. 5 depicts a schematic of the laboratory equipment set-up 10 in which the homogeneous catalytic oxidation of organic substrates in $CO_2$-expanded solvents was carried out. A 10 mL, stainless steel cylindrical cell 12 (18 mm i.d.×18 mm length) fitted with end caps equipped with sapphire windows functioned as the reactor. The cell 12 body had four ports. One of the ports was used to introduce $O_2$ and the solvent medium, $CO_2$, each of which was passed through separate lines and joined in a common line just prior to the port. Oxygen was introduced via a mass flow controller 14 (5860E, Brooks Instruments), capable of regulating flow rates in the 0–120 sccm range. Liquid $CO_2$ was pumped from a cylinder to a reservoir 16 and then passed through a bed 18 of anhydrous calcium sulfate (Drierite) to remove any moisture from the $CO_2$ before introducing it into the cell 12. The second port was used for injecting liquid into the cell 12 and was connected to a safety head containing a rupture disc. A pressure transducer 20 and a thermocouple 22 were connected at the remaining two ports; the fifth port is used for releasing the reaction mixture for sampling. The cell 12 was designed to withstand pressures and temperatures up to 340 bar and 350° C. A magnetic stirrer 24 provided mixing of the reactor contents. Fiber optics interfaced with a PC2000 UV-Vis Spectrophotometer (Ocean Optics) provided in situ temporal measurements of catalyst activity and reactant concentrations, when feasible.

For reaction studies, known amounts of a substrate and catalyst were initially charged into the cell 12. The cell 12 was closed, and a liquid solvent was metered through the top port with a syringe. A heating tape wrapped around the cell provided the heating source. Next, liquid $CO_2$ was pumped from the cylinder into the cell 12 to a pressure that was less then the ultimate operating pressure. The contents of the cell 12 were then stirred while simultaneously warming the cell 12 to the desired reaction temperature. With the help of the mass flow controller 14, a predetermined amount of ultra high purity oxygen was charged to the cell, raising the cell pressure closer to the operating pressure. Finally, $CO_2$ was introduced as necessary to reach the desired expansion. The reaction time was counted beginning with the moment at which the operating cell expansion was reached. A data acquisition system (Camile® TG, Sagian) connected to a computer was utilized for continuous control and/or monitoring of cell temperature, cell pressure, and $O_2$ flow rate. After a predetermined reaction time, the cell pressure was gradually released (over 2 hours) while transferring the cell contents into a cold trap containing an organic solvent, e.g. methylene chloride. Following depressurization, the cell was thoroughly washed with several injections of methylene chloride. The trapped and washed cell contents were mixed, and an external standard such as toluene was added. The mixture was further diluted with methylene chloride to 100 mL. Aliquots of the diluted samples were then transferred into vials and analyzed by GC/FID and/or GC/MS. A carbon balance determination indicates only up to about 5% material loss during the process.

The experimental conditions, conversions, and selectivities for the oxidation of DTBP by CO(salen*) in neat $CH_2Cl_2$, $scCO_2$, and $CO_2$-expanded-$CH_2Cl_2$ are given in Table 2. In the reaction medium, the molar concentrations of the catalyst and the substrate were held constant. The low solubility of oxygen in neat $CH_2Cl_2$ limited the molar ratio of oxygen:substrate to a maximum of 2 while the ratio was 10 for the other two media. Due to the low boiling point of $CH_2Cl_2$ (40° C.), the reaction carried out in the neat $CH_2Cl_2$ could only be performed at lower temperatures (approximately ambient temperature, 25° C.). At the given concentrations of reaction components, the conversion at 25° C. established a baseline for the maximum possible DTBP conversion and DTBQ selectivity in neat $CH_2Cl_2$. The reaction time in the $scCO_2$ was kept to 21 h as the conversion was smaller in just 2 hrs.

TABLE 2

Comparison of DTBP conversion and DTPQ selectivity during DTBP Oxidation with Co(salen*) complex in $CH_2Cl_2$, $CO_2$-expanded $CH_2Cl_2$ (roughly two-fold volumetrically), and $scCO_2$ Media[a]

| Medium | P(total) bar | Temp ° C. | Time (hrs) | $CH_2Cl_2$ mL | Molar $O_2$:Substrate | Conv. % | DTPQ Select % |
|---|---|---|---|---|---|---|---|
| $CH_2Cl_2/O_2$ | 2.8 | 25[b] | 2 | 10 | 2 | 17 | 88 |
| $scCO_2$ | 207 | 70 | 21 | 0 | 10 | 80 | 70 |
| $CH_2Cl_2/CO_2$ | 62 | 70 | 2 | 5 | 10 | 99 | 98 |

[a]Reaction conditions: substrate (68 mg); catalyst (2.5 mg); methyl imidazole (2 μL) and total reaction volume of 10 mL.
[b]Boiling point of $CH_2Cl_2$ is 40° C.

As shown in Table 2, the total DTBP conversion and DTBQ selectivity of products in the $CO_2$-expanded solvent medium (from 5 mL initially to 10 mL by $CO_2$) were far better than corresponding values in the $scCO_2$ medium and neat $CH_2Cl_2$ media. While the DTBP conversion in the $CO_2$-expanded $CH_2Cl_2$ was nearly complete, it was only around 20% and 80% complete in the neat $CH_2Cl_2$ and $scCO_2$ media, respectively. This was true even though the reaction time in the case of the $scCO_2$ medium was more than ten times that of the other two media. Hence, the $CO_2$-expanded $CH_2Cl_2$ media clearly demonstrated its superiority as the reaction medium in the oxidation process. In addition to the above characteristics, the higher operating temperatures allowable with the $CO_2$-expanded solvent may be exploited to attain high conversions and superior selectivity at significantly lower batch times.

Figure 6:
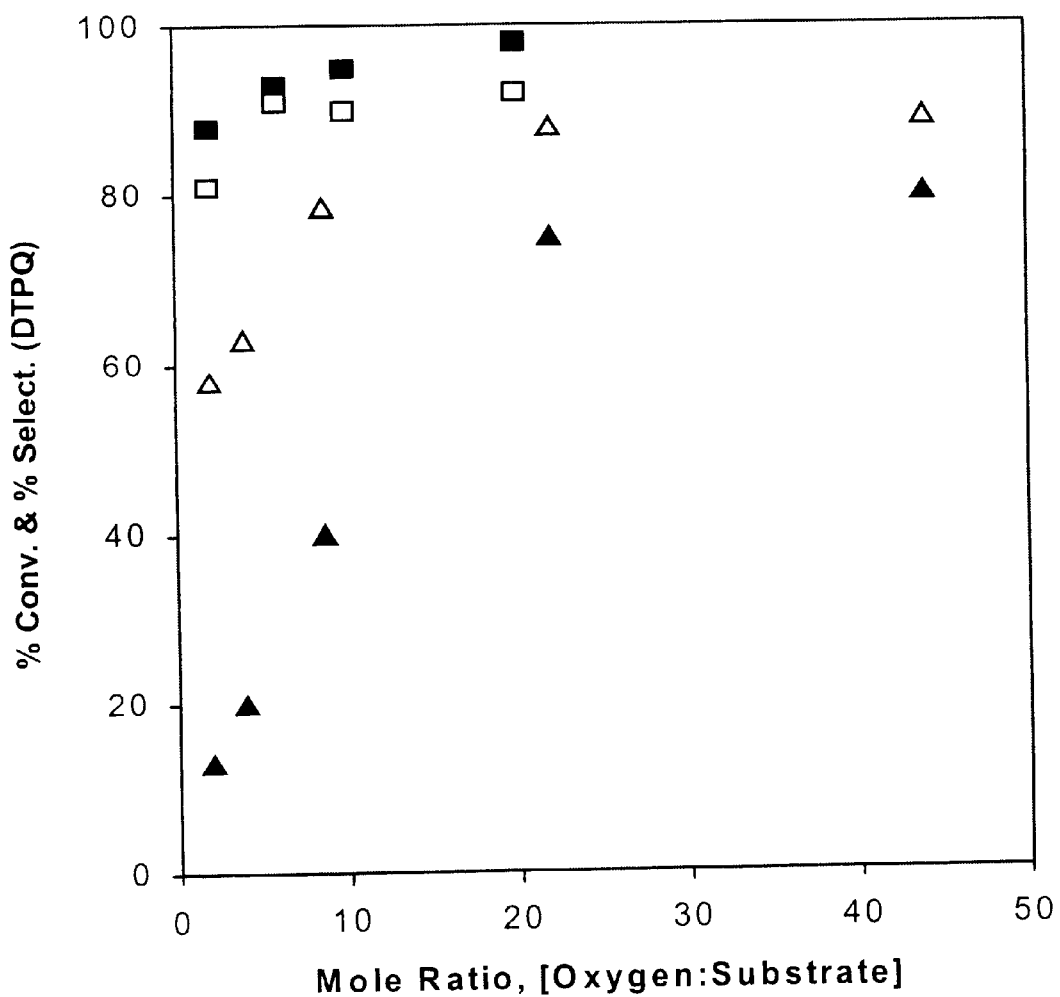
FIG. 6 is a graph comparing 2,6-di-tert-butylphenyl (DTBP) conversion and 2,2-di-tert-butylquinone (DTBQ) selectivity obtained with Co(salen) at different oxygen:substrate molar ratios.
Figure 7:
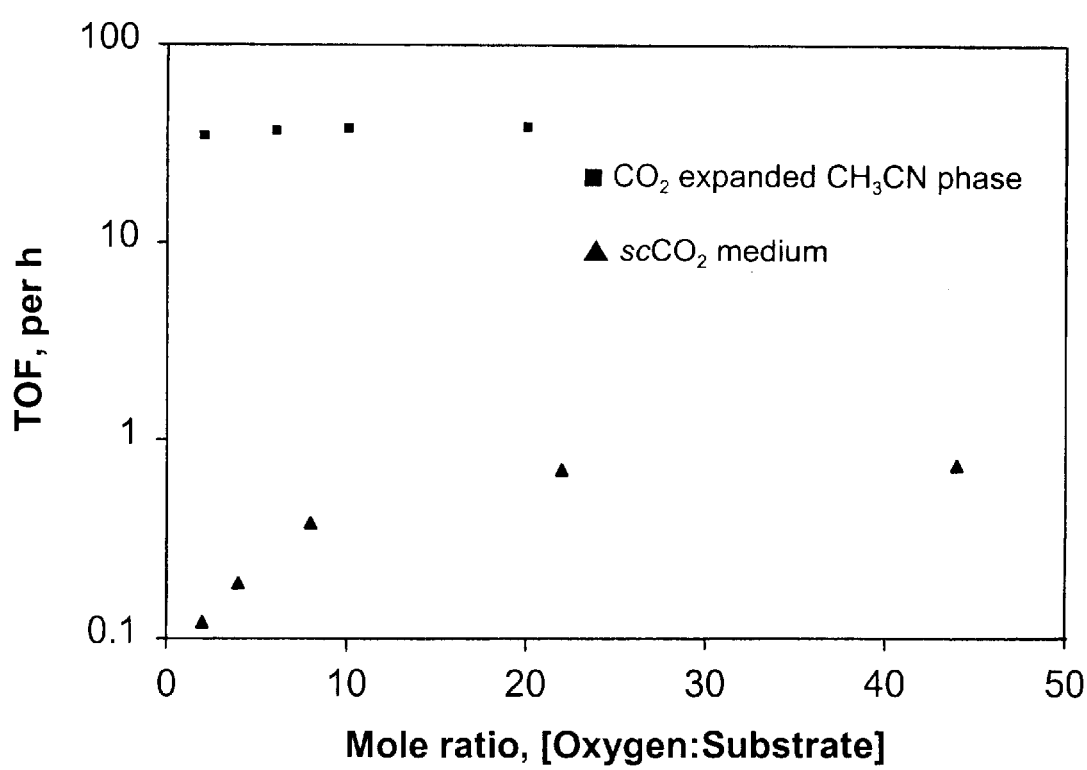
FIG. 7 is a graph comparing the turnover frequency (TOF), at various oxygen:substrate molar ratios, in a two-fold, $CO_2$-expanded $CH_3CN$ phase and in a supercritical $CO_2$ medium.

The effects of oxygen concentration on selectivity and total conversion during DTBP oxidation in $CO_2$-expanded $CH_3CN$ and $scCO_2$ reaction media are compared in FIG. 6. At 60° C., conversion and selectivity in the $CO_2$-expanded-$CH_3CN$ solvent were always higher than in $scCO_2$ reaction medium. As shown in FIG. 6, the difference in conversion between the two solvent systems was even more pronounced at lower oxygen concentrations. This is even better observed in FIG. 7. The turnover frequency (TOF—defined as moles of substrate converted per mole of catalyst per hour of batch time) for the oxidation rate in the $CO_2$-expanded phase was at least forty times higher than the oxidation rate in $scCO_2$ medium. The TOF enhancement was more than two orders of magnitude at lower $O_2$ concentrations.

Figure 8:
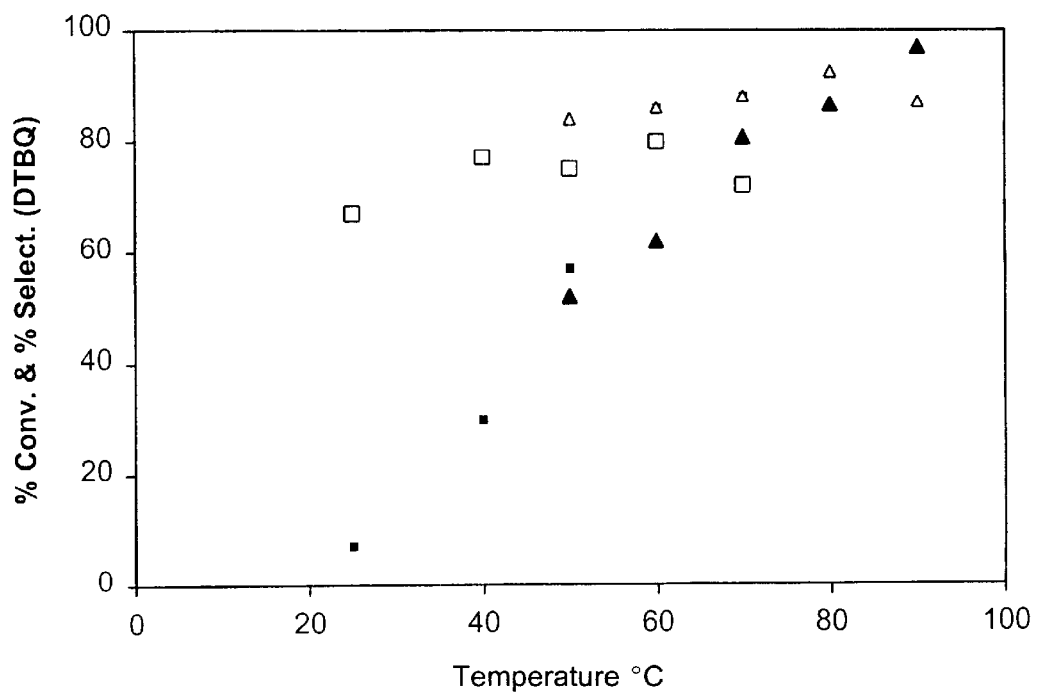
FIG. 8 is a graph comparing DTBP conversion and DTBQ selectivity obtained with Co(salen) complex at different temperatures.
Figure 9:
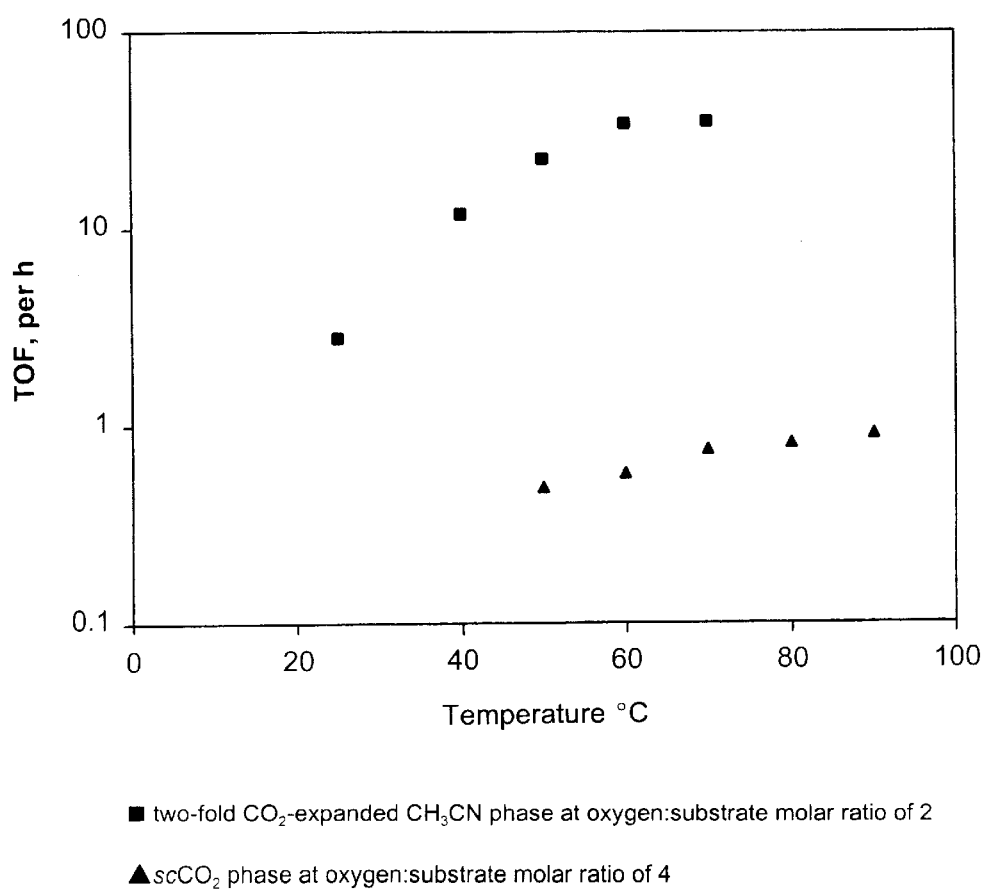
FIG. 9 is a graph depicting the TOF versus reaction temperature in a two-fold, $CO_2$-expanded $CH_3CN$ phase and in a supercritical $CO_2$ phase.

As shown in FIGS. 8 and 9, similar significant enhancements (higher DTBP conversion, DTPQ selectivity, and TOF's with the $CO_2$-expanded solvent phase) were also observed with respect to the temperature dependency.

Figure 10:
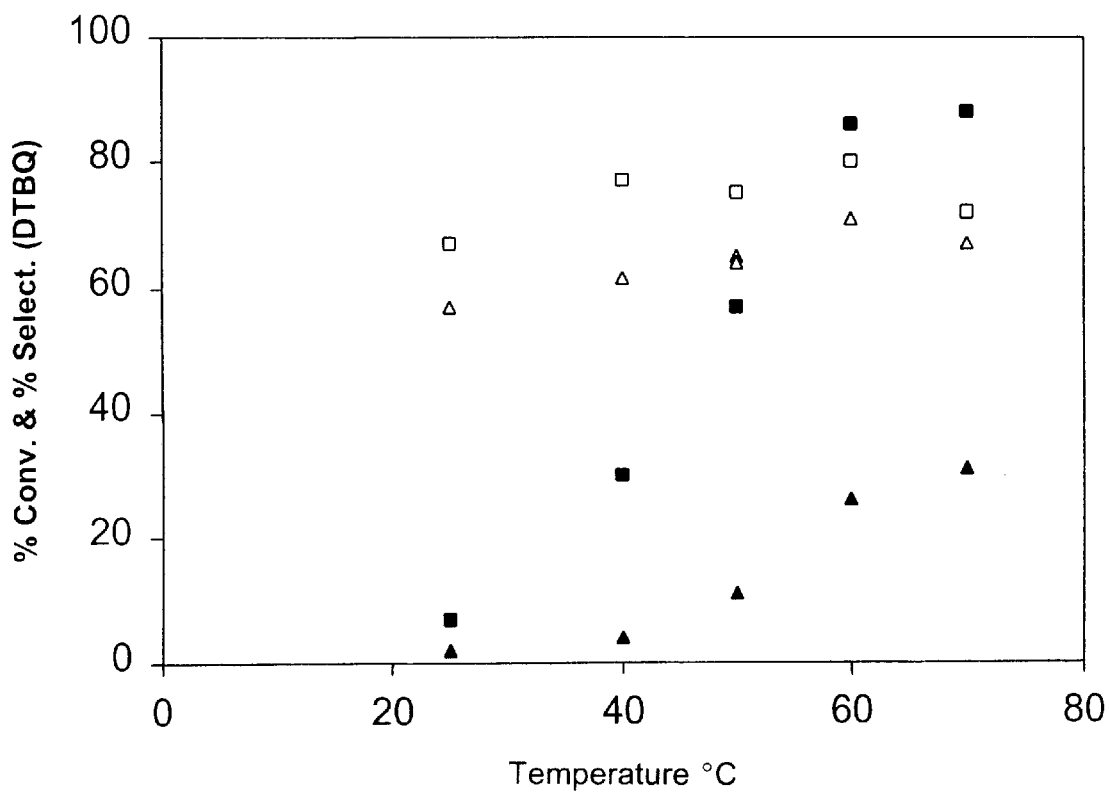
FIG. 10 is a graph comparing the conversion and selectivity of DTBP oxidation at different temperatures and with different catalysts.

FIG. 10 compares the DTBP conversion and DTBQ selectivity obtained with Co(salen) and Co(salen*) catalysts in $CO_2$-expanded solvent media. As summarized in Table 3, Co(salen*) is significantly more active than Co(salen) both in terms of conversion and selectivity at the various oxygen:substrate molar ratios. It is expected that Co(salen*) is intrinsically more active than co(salen) for catalytic oxidations with molecular oxygen. Oxidations in the $CO_2$-expanded solvent, wherein the $O_2$ solubility in the reaction medium is not a limitation, clearly brings out this effect. Table 4 sets forth the supplementary experimental conditions for the data depicted in FIGS. 6–10.

TABLE 3

Comparisons in the Oxidation of DTBP by Co(salen) and Co(salen*) Complexes in Two Fold Expanded $CO_2$ Medium

| | Co(salen*) | | Co(salen) | |
|---|---|---|---|---|
| $O_2$:Substrate | % Conv. | % Select | % Conv. | % Select |
| 2 | 88 | 81 | 10 | 64 |
| 6 | 93 | 91 | 12 | 57 |
| 10 | 95 | 90 | 14 | 43 |

TABLE 4

Supplementary Experimental Conditions for the Data Represented in FIGS. 6–10[a]

| Figure | Reaction Media | p bar | time (hrs) | T ° C. | Molar ratio $O_2$:Substrate | $CH_3CN$ mL |
|---|---|---|---|---|---|---|
| 6 | $CO_2$-expanded $CH_3CN$ | 62 | 2 | 60 | — | 5 |
| 6 | $scCO_2$ | 207 | 21 | 70 | — | — |
| 8 | $CO_2$-expanded $CH_3CN$ | 42–69 | 2 | — | 2 | 5 |
| 8 | $scCO_2$ | 207 | 21 | — | 4 | — |
| 10 | $CO_2$-expanded $CH_3CN$ | 42–69 | 2 | — | 2 | 5 |

[a]All the reactions were carried out in 10 mL reactor with 4.1 mmol of catalyst and 2 μL of methyl imidizole.

Example 3

Oxidation of Alkenes

The typical experimental conditions, conversions, and selectivities for the oxidation of cyclohexene by PFTPPFeCl in neat $CH_3CN$, $scCO_2$, and $CO_2$-expanded $CH_3CN$ reaction media are given in Table 5 (see also Scheme 2). The reaction in the first two media were reported by Tumas et al. (see Birnbaum et al., Metalloporphyrin-Catalyzed Homogeneous Oxidation in Supercritical Carbon Dioxide, *J. Mol. Catal.*, 139:11–24 (1999). Rows 1, 4, and 5 of Table 5 represent data reported by Birnbaum et al. The data in rows 2 and 3 of Table 5 represents conversion and selectivity results obtained in $CO_2$-expanded $CH_3CN$ according to the invention. The reaction in the $CO_2$-expanded solvent was performed at lower temperatures (25° C.) as compared to 80° C. in the case of neat solvent and supercritical $CO_2$ reaction media. GC/MS analysis revealed that the oxidation in the $CO_2$-expanded solvent medium produced five products: cyclohexene oxide, 1,2-cyclihexanediol, 2-cyclohexene-1-ol, 2-cyclohexene-1-one, and 4-hydroxy-2-cyclohexene-1-one. While the first two products are produced by O-atom transfer, the rest are produced by a mechanism which involves an allylic H-abstraction. The 1,2-cyclihexanediol is produced as a result of the subsequent hydration of cyclohexene oxide. Hence, in a perfectly dry analysis environment, the hydration could be avoided, and a higher yield of the unhydrated epoxide would result. Importantly, reactions in neat $CH_3CN$ and $scCO_2$ (Birnbaum et al.) media do not produce measurable 1,2-cyclihexanediol. Birnbaum et al. reported a product (oxabicyclo [4.1.0]heptan-2-one) that was not seen in measurable amounts in the instant $CO_2$-expanded $CH_3CN$ media tests. Since this product is only partly produced by other routes not involving cyclohexene oxide, the epoxide selectivity as a primary product was still lower than that of the cyclohexene oxide.

Scheme 2

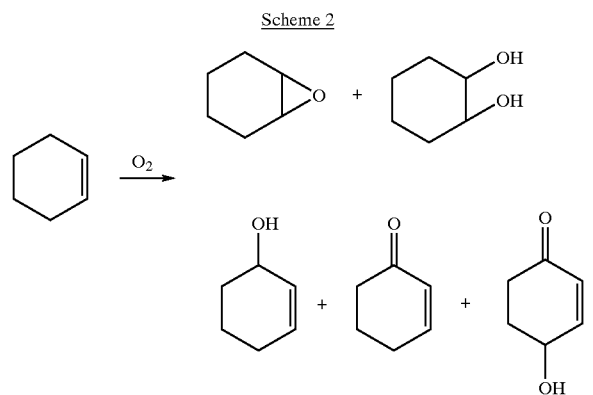

Catalyst = PFTPPFeCl

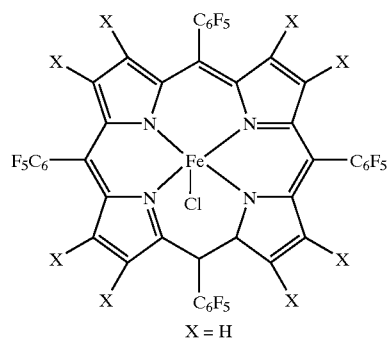

X = H

TABLE 5

Comparision of Cyclohexene Oxidation by PFTPPFeCl in $CH_2Cl_2$, $CO_2$-expanded $CH_3CN$ (roughly two-fold volumetrically), and $scCO_2$ Media

| T (° C.) | Time (hrs.) | p bar | Conv. % | Oxide % | Diol % | Enol % | Enone % | Enoneol % |
|---|---|---|---|---|---|---|---|---|
| 80[a,1] | 12 | 345 | 32 | 15 | — | 6 | 42 | 6 |
| 25[b,2] | 7 | 48 | 5.2 | 50 | 28 | 7 | 13 | trace |
| 80[d,2] | 4 | 90 | 39 | 35 | 37 | 17 | 4 | 7 |
| 80[c,1] | 4 | 345 | 5.5 | 19 | — | 11 | 45 | 2.2 |
| 80[c,1] | 12 | 345 | 9.0 | 17 | — | 5.5 | 38 | 2.6 |

[a]Reaction performed in $CH_3CH$; catalyst (5 mg); $O_2$: Substrate ratio (1:5); Substrate (500 µL); and total reaction volume (18 mL).
[b]Reaction performed in two-fold $CO_2$-expanded $CH_3CN$; catalyst (2.5 mg); $O_2$; Substrate ratio(2); Substrate (30 µL); and total reaction volume (10 mL).
[c]Reaction performed in $scCO_2$; catalyst (5 mg); $O_2$: Substrate ratio (1:5); Substrate (500 µL); and total reaction volume (18 mL).
[d]Reaction performed in two-fold $CO_2$-expanded $CH_3CN$; catalyst (3 mg), $O_2$:substrate ratio (1.5:2), substrate (500 µL) and $CH_2CN$ (5 mL), and total reaction volume (10 mL).
[1]Birnbaum et al.
[2]According to the instant invention.

As shown in Table 5, the combined selectivity for cyclohexene oxide and 1,2-cyclihexanediol in the $CO_2$-expanded $CH_3CN$ was more than 70% compared to less than 20% in either the $scCO_2$ or neat $CH_3CN$ media. Significantly, the superior selectivity was obtained at significantly lower temperatures, pressures, and reaction times. In addition, the overall conversion is highest in expanded-phase oxidation at 80° C. In addition to the TFPPFeCl catalyst, oxidation of cyclohexene in $CO_2$-expanded-$CH_3CN$ medium by porphyrin and Schiff base complexes of Co(II), Ru(II) and Mn(II) was also obtained.

Example 4

Figure 11:
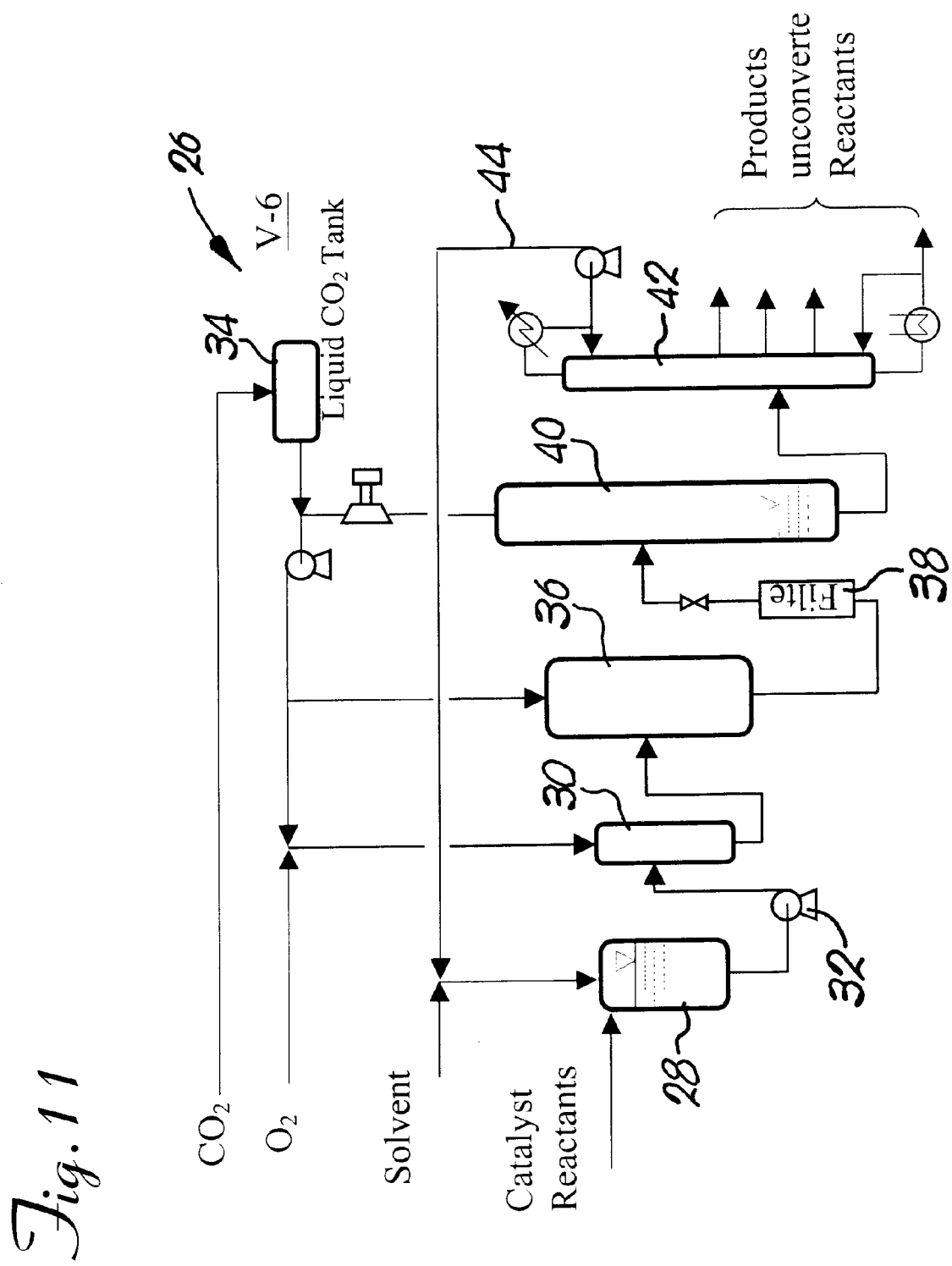
FIG. 11 is a schematic illustration of a process flow for a batch process according to the invention.

Batch Process for Catalytic Oxidation of Organic Substrates in $CO_2$-Expanded Organic Solvents FIG. 11 depicts the essential scheme 26 of a batch process for the catalytic oxidation of organic substrates in $CO_2$-expanded organic solvents using molecular oxygen as the terminal oxidizing agent. A catalyst, transition metal complex, and organic substrate to be oxidized are measured and dissolved in organic solvents in vessel 28. The resulting solution is then transferred to a high pressure reactor 30 via a pump 32. Oxygen is metered and introduced to the reactor 30, while liquid $CO_2$ is pumped from a reservoir 34 into the reactor 30. The reaction is then quenched by transferring the reaction mixture from the reactor 30 to a vessel 36. Additional liquid $CO_2$ is pumped into vessel 36 causing the catalyst to precipitate. The precipitated solid catalyst is preferably separated from the liquid mixture by filtration through filter 38. The filtrate is transferred to a vessel 40 by decreasing pressure. The mixture attains two phases. That is, the $CO_2$ becomes a gas, and the reaction mixture remains in the organic solvent in the liquid state. The gaseous $CO_2$ is then compressed into a liquid and recycled for another cycle. The organic solution is transferred into a distillation column 42 for separation and purification. The organic solvent is collected and recycled (arrow 44) for reuse in the process.

The oxidation products and unconverted organic substrates are separated by distillation or other methods. Vacuum distillation can be utilized to decrease the operation temperature if the oxidation products are heat-sensitive.

Vessels 30 and 36 are high-pressure vessels, with the maximum pressure rate for these vessels being about 120 bar. The maximum operating temperature of the reactor 30 is about 250° C. Vessels 28, 36, and 40 operate at ambient temperatures. The operation temperatures of the distillation column 42 is dependent upon the organic solvents, the composition of the oxidation products, and the operation pressure.

Example 5

Figure 12:
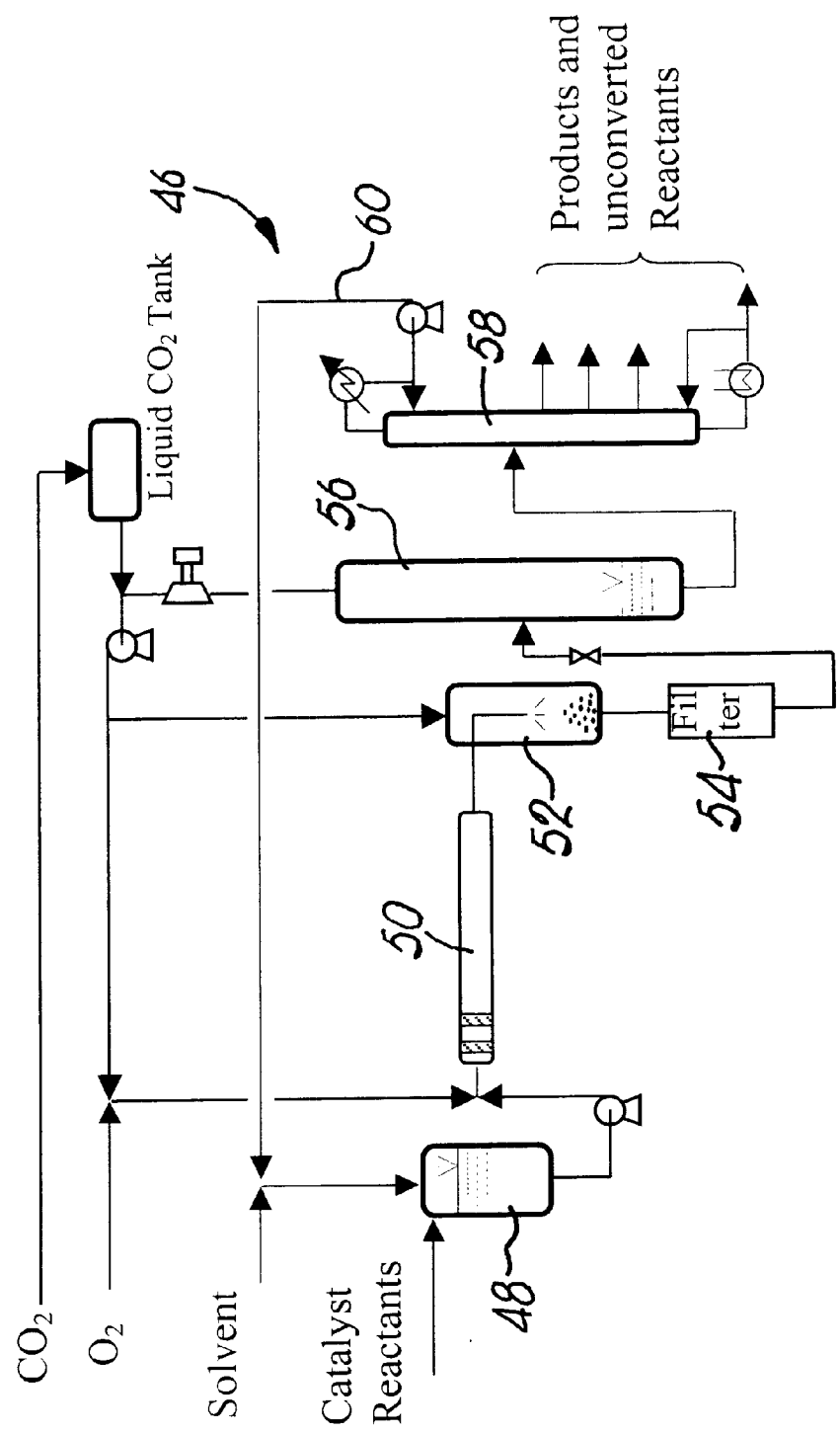
FIG. 12 is a schematic illustration of a process flow for a continuous process according to the invention.

Continuous Process for Catalytic Oxidation of Organic Substrates in $CO_2$-Expanded Organic Solvents FIG. 12 depicts a schematic 46 of the essential equipment of a continuous process for the catalytic oxidation of organic substrates in $CO_2$-expanded organic solvents using molecular oxygen as the oxidizing agent. A catalyst, transition metal complex, and the organic substrate to be oxidized are measured and dissolved in organic solvents in vessel 48. The solution is then pumped to high pressure, mixed with $CO_2$ and $O_2$, and introduced into a tube reactor 50. A static mixer is employed for optimal mixing of the streams. The flow rate of the stream through the tube reactor 50 is controlled for a suitable reaction time.

The reaction is then quenched by directly spraying the reaction mixture into downward-flowing liquid $CO_2$ in vessel 52, causing the catalyst to precipitate. The precipitated solid catalyst is preferably separated from the liquid mixture by filtration through filter 54. The filtrate is transferred to vessel 56 by decreasing pressure. The mixture attains two phases. That is, the $CO_2$ becomes a gas, and the reaction mixture remains in the organic solvent in the liquid state. The gaseous $CO_2$ is then compressed into a liquid and recycled for another cycle. The organic solution is transferred into a distillation column 58 for separation and purification. The organic solvent is then collected and recycled (see arrow 60) for reuse. The oxidation products and unconverted organic substrates are separated by distillation or other methods. Vacuum distillation can be utilized to decrease the operating temperatures if the oxidation products are heat-sensitive.

Tube 50 and vessel 52 are high pressure vessels having maximum pressure rates of about 120 bar. The maximum operating temperatures of the reactor should be about 250° C. Tube 50 and vessels 52, 56 operate at ambient temperatures. The operating temperature of the distillation column 58 is dependent upon the organic solvents, composition of the oxidation products, and operating pressure.

DISCUSSION

In light of the foregoing test data, it is clear that the instant invention provides significant advantages over the prior art. First, the inventive process is applicable to a wide range of oxidation catalysts and substrates. That is, a wide range of conventional transition metal complexes (e.g., Schiff bases, porphyrin metal complexes) catalyze the oxidation of organic substrates (including alkenes and phenols) in $CO_2$-expanded reaction media at significant conversion rates. Furthermore, the selectivity of the oxidation process toward the desired product(s) is significantly improved as compared to the selectivity of oxidation products in conventional organic solvents.

Another significant advantage of the inventive process is the reduced use of conventional organic solvents which present both environmental and safety hazards. $CO_2$ is non-toxic, non-flammable, inexpensive, and recyclable and has a relatively low critical temperature (31.1° C.) and a moderate critical pressure (73.8 bar). Thus, $CO_2$ behaves as an environmentally-benign cosolvent. By replacing a significant portion (e.g., up to about 80%) of the organic solvent on a volume basis with supercritical or subcritical $CO_2$, the inventive process results in a significantly reduced use of conventional solvents, thus resulting in a process which is more environmentally friendly than prior art processes.

Another significant advantage of the instant invention is that lower operating pressures are required than is the case with prior art supercritical $CO_2$-based reaction systems. The solvent is expanded with $CO_2$ to such an extent that the amount of the catalyst and the substrate dissolved in the $CO_2$-expanded solvent mixture is more or less the same when compared to the neat solvent medium. That is, while the catalyst and the substrate are both soluble in the neat solvent, it is not necessary that either the substrate or the catalyst be soluble in subcritical or supercritical $CO_2$ as is true with prior art supercritical $CO_2$-based processes. In those processes, the minimum solubilization pressures for transition metal catalysts in supercritical $CO_2$ are very high (on the order of several hundred bars). However, the process of the present invention provides for oxidation reactions in $CO_2$-expanded solvents to be performed at relatively low pressures (on the order of several tens of bars).

The invention also provides the benefit of increased oxygen solubility in the reaction mixture when compared to the neat solvent medium. This is particularly beneficial in situations where oxygen solubility in the substrate or oxygen transport to the catalyst is the rate-determining step.

The inventive processes are also much safer than the prior art processes in neat organic solvents because the vapor pressure of the reaction medium is significantly lower when compared to reactions in unexpanded solvents at ambient pressures. This allows for reaction temperatures which are tens of degrees higher than upper temperature limit of the corresponding neat solvent system. Operation at these higher temperatures significantly enhances the reaction rate—by several orders of magnitude—without decreasing product selectivity. This is significantly improved over prior art reactions in neat solvent systems where the upper temperature limit is constrained by the boiling points of the solvent and substrate at ambient pressure. At around this temperature, partial evaporation of the solvent can occur, leading to supersaturation of the solution and subsequent precipitation of the reaction components adversely affecting the reaction rate and selectivity. Furthermore, the organic vapors generated at higher operating temperatures can form explosive mixtures with the oxidant leading to unsafe operating conditions. Hence, the prior art reactions are typically carried out at a temperature at which the vapor pressure of the organic solvent is low. In many cases, this leads to very low reactions rates requiring longer batch times or larger reactor volumes during continuous processing.

The presence of $CO_2$ in the reaction mixture significantly ameliorates the flammibility of the reaction mixture. Furthermore, the greater oxidation rates at higher temperatures result in reduced reactive volumes or less "hold-up" of substrates in a reactive environment. Finally, the heat capacity of the reaction mixture is more "liquid-like" which allows the reaction mixture to effectively absorb the heat of reaction and limit adiabatic temperature rise within safe limits. One further advantage of the inventive process is the fact that the reactants, catalyst, and products can be readily separated and/or purified. For example, the solid catalysts can be precipitated out of the reaction mixture by simply adding more $CO_2$ to the reaction mixture. With reliable knowledge of the phase behavior of the reaction mixture, the catalyst-free reaction mixture may then be subjected to step-wise pressure reduction to effect the separation of the product(s) and remaining reactants based upon the principles of supercritical fluid chromatography. The recovered catalyst and $CO_2$ can then be recycled back into the process.

We claim:

1. A reaction mixture comprising a substrate to be oxidized, an oxidation catalyst, an organic solvent system with said substrate and catalyst solubilized in the solvent system, and a sufficient quantity of a compressed gas comprising a gas selected from the group consisting of carbon dioxide, $N_2O$, Xenon and $SF_6$ to volumetrically expand the reaction mixture, as compared with the volume thereof without said gas therein, said reaction mixture having an increase in volume relative to the volume without said gas therein ($\Delta V/V_0$) of from 0.18–5.0.

2. The reaction mixture of claim 1, said substrate being a liquid oxidizable substrate.

3. The reaction mixture of claim 1, said volumetrically expanded reaction mixture having a lower density, as compared with said reaction mixture without said gas therein.

4. The reaction mixture of claim 1, said gas being carbon dioxide.

5. The reaction mixture of claim 4, said carbon dioxide being introduced at supercritical conditions for the carbon dioxide.

6. The reaction mixture of claim 1, said gas being present at a level to maintain said catalyst suspended in the reaction mixture.

7. The reaction mixture of claim 1, wherein said substrate is selected from the group consisting of the phenols, alkenes, cycloalkenes, alkanes and alcohols, and mixtures thereof.

8. The reaction mixture of claim 1, wherein said substrate is cyclohexene.

9. The reaction mixture of claim 1, said reaction mixture including an organic solvent system comprising a solvent selected from the group consisting of acetonitrile, methylene chloride, dimethyl sulfoxide, acetone, hexane, chloroform, toluene, dichloroethane and mixtures thereof.

10. The reaction mixture of claim 1, said catalyst selected from the group consisting of transition metal complexes of Fe, Mn, Co, Cu, Ni, V, Cr, Mo, W, Re, Ru, and Rh and mixtures thereof.

11. The reaction mixture of claim 1, wherein said catalyst is selected from the group consisting of Co(salen*), Co(salen), and PFTPPFeCl.

12. The reaction mixture of claim 1, said oxidizing agent being selected from the group consisting of air, oxygen, ozone, $N_2O$ and mixtures thereof.

13. The reaction mixture of claim 1, wherein said reaction mixture is maintained in a closed system at superatmospheric pressure.

14. The reaction mixture of claim 1, said reaction mixture being under a pressure of from about 20–250 bar during said introducing and oxidizing steps.

15. The reaction mixture of claim 1, said reaction mixture having a temperature of from about −70 to 250° C.

16. A reaction mixture comprising an oxidizable substrate, an oxidation catalyst for the substrate, an organic solvent system with said substrate and catalyst solubilized therein, and a quantity of compressed gas selected from the group consisting of $CO_2$, $N_2O$, Xenon and $SF_6$ sufficient to volumetrically expand the reaction mixture, as compared with the volume of the reaction mixture without said gas therein.

17. The reaction mixture of claim 16, said gas being an oxidizing agent for said substrate.

18. The reaction mixture of claim 16, including an oxidizing agent in said reaction mixture separate from said gas.

19. The reaction mixture of claim 16, said gas being carbon dioxide.

20. The reaction mixture of claim 16, said gas being present at a level to maintain said catalyst suspended in the reaction mixture.

21. The reaction mixture of claim 16, wherein said substrate is selected from the group consisting of the phenols, alkenes, cycloalkenes, alkanes and alcohols, and mixtures thereof.

22. The reaction mixture of claim 16, wherein said substrate is cyclohexene.

23. The reaction mixture of claim 16, said reaction mixture including an organic solvent system comprising a solvent selected from the group consisting of acetonitrile, methylene chloride, dimethyl sulfoxide, acetone, hexane, chloroform, toluene, dichloroethane and mixtures thereof.

24. The reaction mixture of claim 16, said catalyst selected from the group consisting of transition metal complexes of Fe, Mn, Co, Cu, Ni, V, Cr, Mo, W, Re, Ru, and Rh and mixtures thereof.

25. The reaction mixture of claim 24, wherein said catalyst is selected from the group consisting of Co(salen*), Co(salen), and PFTPPFeCl.

26. The reaction mixture of claim 16, wherein said reaction mixture is maintained in a closed system at superatmospheric pressure.

27. The reaction mixture of claim 16, said reaction mixture being under a pressure of from about 20–250 bar.

28. The reaction mixture of claim 16, said reaction mixture having a temperature of from about −70 to 250° C.

* * * * *